United States Patent [19]

Staffolani

[11] 4,220,712
[45] Sep. 2, 1980

[54] DENTAL IMPLANT AND METHOD OF INSERTING

[75] Inventor: Nicola Staffolani, Perugia, Italy

[73] Assignees: Pantomedical Grifo S.A.S.; Nicola Staffolani, both of Perugia, Italy

[21] Appl. No.: 883,841

[22] Filed: Mar. 6, 1978

[51] Int. Cl.² ............................................. A61C 8/00
[52] U.S. Cl. .................................... 433/173; 433/141
[58] Field of Search ............... 32/10 A; 433/173, 174, 433/175

[56] References Cited

U.S. PATENT DOCUMENTS

| | | | |
|---|---|---|---|
| 2,721,387 | 10/1955 | Ashuckian | 32/10 A |
| 2,745,180 | 5/1956 | Kiernan, Jr. | 32/10 A |
| 3,497,953 | 3/1970 | Weissman | 32/10 A |
| 3,738,008 | 6/1973 | Edelman | 32/10 A |
| 3,827,145 | 8/1974 | Richards | 32/10 A |
| 3,955,280 | 5/1976 | Sneer | 32/10 A |

FOREIGN PATENT DOCUMENTS 540713  3/1956  Italy ......................................... 32/10 A

*Primary Examiner*—Louis G. Mancene
*Assistant Examiner*—John J. Wilson
*Attorney, Agent, or Firm*—LWigman & Cohen

[57] ABSTRACT

The present invention relates to a method and an apparatus for obtaining an artificial alveolus for a pin with a spheric head supporting at least one tooth root or, in connection with a similar device, a bridge carrying more teeth, the apparatus being provided with at least one root assembly. The artificial alveolus is formed by a body with two portions integral with each other. Between the spheric head pin and the alveolus an elastic covering is provided and is capable of being deformed in order to allow springing and slight oscillations of the spheric head pin with respect to the alveolus. Each root assembly is obtained in a body provided with a vertical threaded bore opened upwards. The lower end of the body extends downwards in a shaped cavity divided in sections forming external triangular tips and internal shaped guide tangs among which a little pin is inserted in order to cause the rotation of the tips outwards, said apparatus consisting of titanium, tantalum or other material that does not give rise to the phenomenon of rejection from the organism.

10 Claims, 6 Drawing Figures

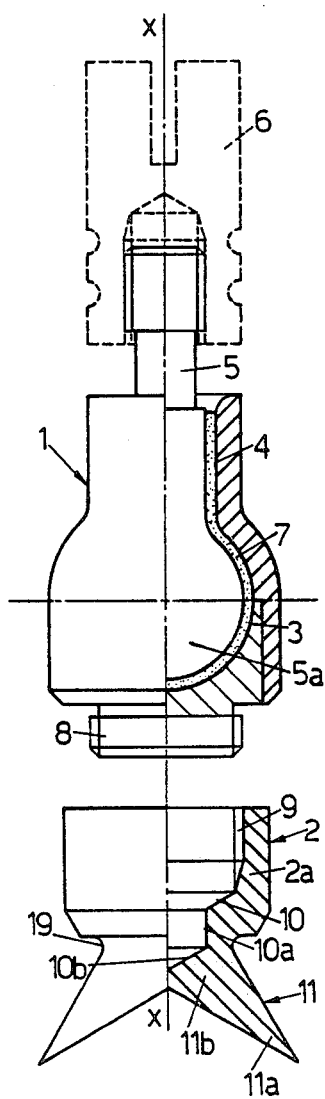
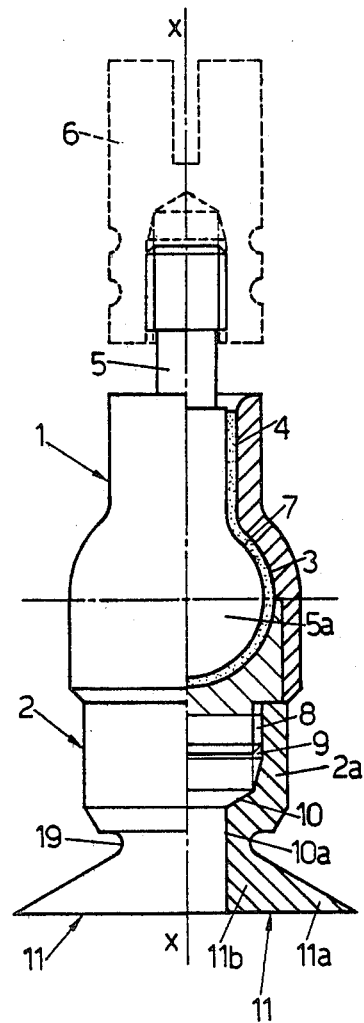
FIG.1
FIG.2

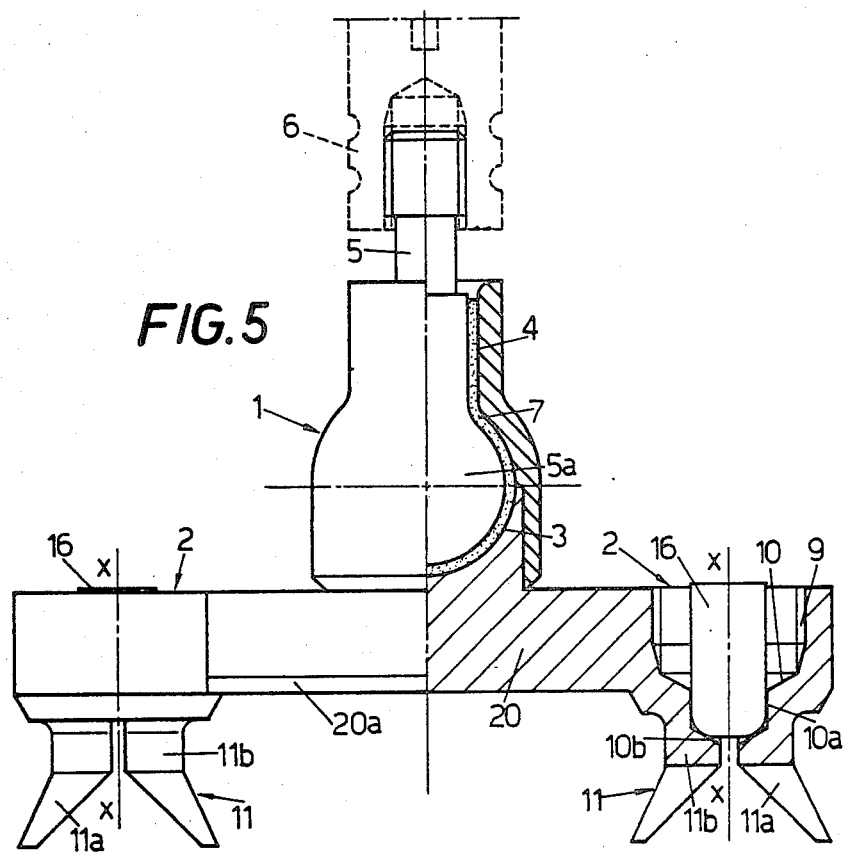
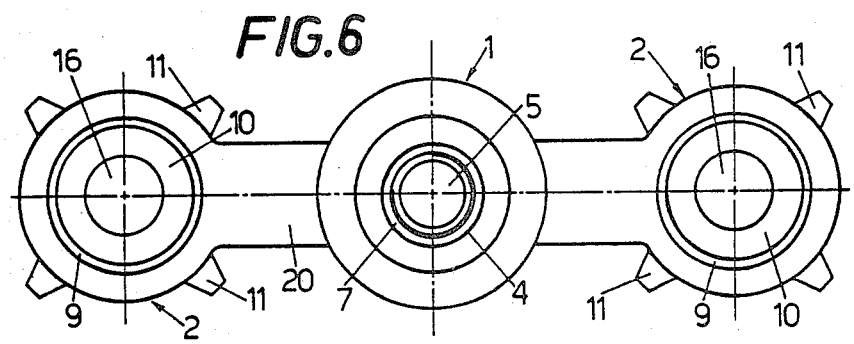

DENTAL IMPLANT AND METHOD OF INSERTING

BACKGROUND AND SUMMARY OF THE INVENTION

The present invention relates to an apparatus for obtaining an artificial alveolus for a pin with a spheric head supporting at least one tooth root or, in connection with a similar device, a bridge carrying more teeth. The apparatus is provided with at least one root assembly with tips that, when inserting, are fitted in the jaw bone. The alveolus includes means for damping the stresses transmitted to the tooth and for allowing only slight oscillations thereof. The apparatus may be adjusted according to the individual requirements. The artificial alveolus consists of a single body so as to have no outside junction line. Each root assembly is formed by a plurality of tips, which number may normally vary from two to five, preferably three to four tips. Before being inserted, the tips have a slight slope to the root assembly axis but, during application, are embedded or fitted in the jaw bone in consequence of the penetration therebetween of a pin that is inserted among shaped guide tangs of the tips and that is passed through suddenly by means of a particular instrument. The present invention relates also to a method of assembling the dental prosthesis as well as to the particular instrument able to carry out the operation.

Therefore, owing to the specific characteristics of the present invention, the apparatus thereof has the advantage of being provided with a totally closed alveolus embodied in the jaw bone, wherein the saliva or other liquid that can pass through the interstice, provided between the pin and the alveolus in order to allow slight oscillations of the tooth as well as a light springing thereof, is prevented from coming into contact with the jaw bone and/or the gum. Such contact can produce infections because of the germs that may be contained in such liquids.

Further, the apparatus of the present invention permits the prosthesis to act like a natural tooth since the stresses transmitted to the tooth are damped and appropriately distributed in relation to the bone in which the apparatus is inserted. This arrangement increases the number of roots in the root assembly in connection with the stressed teeth so that impacts to the tooth are damped and beneficially distributed when the bone is thinner and/or less resistant in consequence of the individual age or nature of the bone, that is, a jaw or mandible. The apparatuses, used up to now in the dental implants such as those of the blade or screw type that are at the present time considered more suitable, have demonstrated that a new bony tissue grows where there was a surgical operation for the dental implant application. Further, it was ascertained that this tissue reformation could never in any way reproduce the normal dental-alveolar characteristics, failing the presence of an alveolar structure and the parodontal ligaments. Furthermore, on the basis of research well known to those skilled in the art, it was ascertained that, after a certain time, but however not greater than 5-7 years, an osseous reabsorption around the planted prosthesis nearly always will take place. This reabsorption is the obvious consequence of the fact that the planted prosthesis is unable to sustain either the masticatory stress or the microshocks that are caused in the oral cavity during speech, swallowing and other voluntary and involuntary movements of the tongue and cheeks.

On the basis of the foregoing experience, according to the present invention, an apparatus was designed that includes an artificial spheric alveolus for a pin supporting the tooth or prosthesis, with the object of protecting the jaw bone and the gum where the dental implants is in communication with the oral cavity. This object is the weak point of the present dental implant technique, which causes the above mentioned reabsorption. It should be noted that the alveolus could have also several forms, such as cylindrical or similar shapes, where they can be allowed by the stresses.

Such an apparatus can be used for implanting either a single tooth or, where necessary, more teeth.

It was also ascertained that the fixing of a dental implant by means of a slow action, e.g., by screwing in a pin, easily causes cracking of the surrounding bony wall. Therefore, the embedding of several tips forming a root assembly was tested and carried out with a nearly instantaneous action. To this end, each tip forming one of the assembly roots is provided with a rear shaped guide tang that extends toward the axis of the root assembly, namely, toward an axial bore that extends from the upper surface and through the root assembly up to the above mentioned tangs. This bore is provided with a thread in order to engage, during the application of the prosthesis, the end of a cylindrical instrument that, in turn, includes a shank over which a little pin is mounted. The diameter of the pin is such that, when it is introduced among the tangs of the root tips, it forces the tips to move and to turn out and upwards so that the tips are embedded substantially radially into the bone.

BRIEF DESCRIPTION OF THE DRAWINGS

These and other features and advantages of the present invention will be more apparent from the following description of two embodiments shown in the annexed drawings, wherein:

FIG. 1 is a partially cutaway side view of the two apparatus portions that are separated from each other according to a first embodiment having only one root assembly;

FIG. 2 is a view similar to FIG. 1 but showing the two portions coupled to each other after the application of the prosthesis;

FIG. 5 is a partially cutaway side view of a second embodiment with two root assemblies; and FIG. 6 is a top plan view of the apparatus of FIG. 5.

DETAILED DESCRIPTION OF THE PREFERRED EMBODIMENTS

Figure 3:
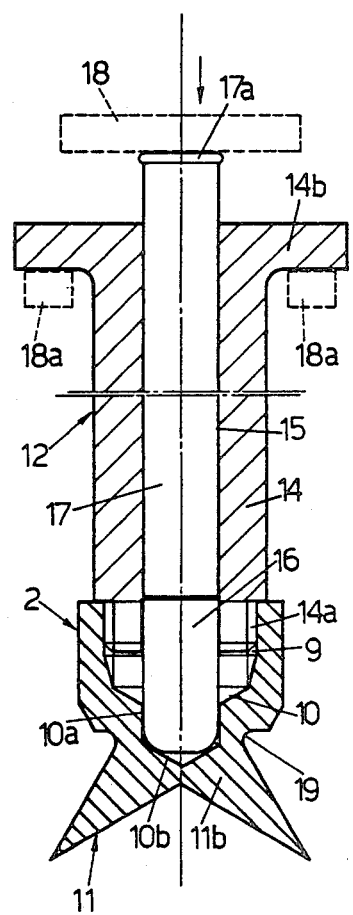
FIG. 3 is an axial section of the portion forming the root assembly that is inserted into the hole provided in the bone after the instrument with the little pin is introduced in order to lock the tips into the bone.

Referring to FIGS. 1 to 4 concerning the first embodiment of the apparatus wherein only one root assembly is provided, the apparatus of the present invention substantially consists of an upper portion 1 and a lower portion 2, the portion 1 comprising a body formed of two pieces that are side welded to each other.

In the portion 1, a spheric alveolus 3 is cut, the form of which may also be different, e.g. elongated, ellipsoidal, or similar. This alveolus extends upwards with a vertical duct 4 in order to form the housing seat of a pin 5 terminating in its lower portion with a spheric head 5a. The pin 5 protrudes from the body 1 with a length that is sufficient for holding means 6 supporting the tooth (not shown) so that the tooth forms an integral part of the pin 5. The spheric head 5a and the pin 5 are covered by an elastomeric material 7 able to support resiliently the alveolus 3 in order to allow slight oscillations of the tooth with respect to the lower portion 2 forming the root assembly, to which the upper portion 1 will be screwed. To this end, the upper portion 1 extends with a cylindrical threaded end 8 that is screwed to a threaded seat 9 cut in the lower portion 2 forming the root assembly.

It should be noted that, instead of covering the pin 5 and its spheric head 5a with an elastomeric material 7, an elastic sheath could also be provided with a sealed interspace filled by a liquid. The external wall of the upper portion 1 in the area above the median plane of the alveolus 3 and the spheric pin head 5a is substantially cylindrical so as to replace almost totally the bone removed for the insertion of the apparatus. Thus, the reformation of new bony tissue is avoided and the dental plant is stabilized and thus exactly fitted in the cavity provided in the bone for housing the prosthesis. The lower portion 2 of the apparatus comprises a cylindrical upper section 2a wherein the threaded seat is provided. The lower portion 2 has an external radius not greater than the maximum external radius of the upper portion 1. The threaded seat or bore 9 extends into a cavity comprising a first conical section 10, a cylindrical section 10a, and a second conical section 10b, whose inverted apex lies on the X—X axis of the apparatus and whose base corresponds with the lower base plane of the cylindrical section 10a. In the illustrated embodiment, three or four tips 11 are formed in the lower portion 2, which can be of triangular, circular, or squared cross section and whose lower edges 11a initially form with the X—X axis of the root assembly an angle not greater than 45° so that the outstanding ends of such tips 11, before assembling, are substantially aligned with the cylindrical external wall of the lower portion 2. Each of the tips 11 forms a tang 11b directed inwards and shaped as a guide cam that substantially extends up to the X—X axis.

The apparatus of the present invention preferably consists of heat treated titanium at least in the area corresponding to the lower portion 2, in order to give greater strength to the material of the tips 11. One can also use tantalum or any other material that offers substantially equivalent strength and does not give rise to the phenomenon of rejection from the organism.

The insertion of the apparatus of FIGS. 1 to 4 occurs as follows.

After an accurate preliminary radiography of the dental arches in order to find the area of thicker bony jaw tissue able to house the prosthesis without damaging the sinuses and the mandible canal, and, furthermore, after evaluation of the more suitable points for fixing the dental plant and the specific characteristics thereof, an apparatus will be applied whose lower portion 2 is provided with two or more tips 11, according to the necessary load that can be sustained by the bone in the concerned area.

An incision of the gingival fibromucous membrane is made in order to uncover the alveolar edge. By means of a drill, a cavity is formed for receiving the apparatus in which the lower portion 2 is to be inserted by embedding the same up to the necessary depth by means of an instrument 12 shown in FIG. 3. Such an instrument 12 is formed by a tubular means 14, the lower portion 14a of which is externally threaded in order to be screwed into the threaded seat 9, while the upper portion thereof is formed by a large grip flange 14b. In the bore 15 of the instrument 12, a little pin 16 is at first inserted and then there is introduced a little shank or stem 17 whose length is such that the portion of its head 17a initially projecting downwards has a length equal to the provided stroke of the pin 16 when it is inserted among the tips 11. This little pin 16 engages the shaped tangs 11b thereof and causes the rotation of the tips 11 out and upwards into the bone. It was demonstrated that the grip of the tips 11 in the bone is effective and does not cause chippings in the bone if the embedding is in practice carried out suddenly.

Figure 4:
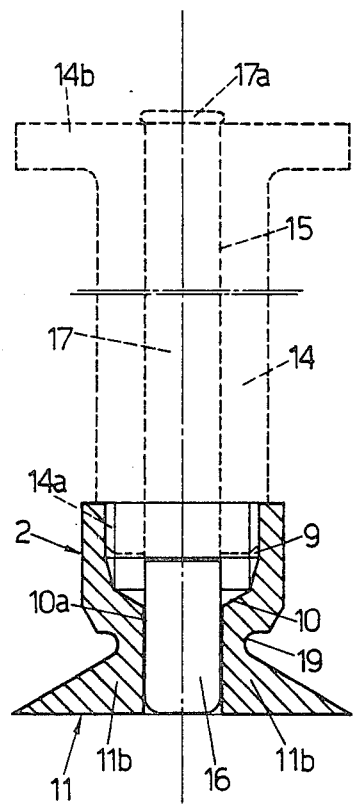
FIG. 4 is a detail of FIG. 3 with the tips of the root assembly embedded into the bone and with the instrument removed, the lower portion of FIG. 3 being ready for the application of the upper portion of the apparatus that includes the alveolus and the pin.

To this end, it is sufficient to use strong dental forceps 18 with two arms 18a, the latter of which is fork-shaped. These arms 18a are inserted under the flange 14b and the outstanding portion of the shank or stem 17 is forced quickly by the forceps 18 on top of the head 17a till the shank or stem 17 is recessed into the bore 15. This action causes the insertion of the little pin 16 among the conically shaped tangs 11b acting as cams and, owing to the movement thereof, forces the tips 11 to rotate out and upwards. The length of the little pin 16 is such that the axial displacement thereof is sufficient to carry out the rotation of the tips 11. Thus, the little pin 16 remains firmly embedded among the tangs 11b, as shown in FIG. 4. On the external surface of the tips 11, notches 19 are formed in the bending area of said tips 11 in order to facilitate the above mentioned operation. The instrument 12 is thereafter removed and the upper portion 1 of the apparatus is screwed in the threaded seat 9 through the threaded end 8. The apparatus is then ready for receiving the holding support means 6 carrying the tooth or a bridge with more teeth.

The second variant shown in FIGS. 5 and 6 is employed when it is necessary to distribute the load acting on the pin 5 with the spheric head 5a over more than one root assembly. Thus, the upper portion 1, that forms the body in which the alveolus receives the pin 5 and its spheric head 5a, is identical to the upper portion 1 of the first embodiment, while the lower portion 2 is integral with a bridge 20 at which ends the threaded seats 9 of each root assembly are formed. The lower portion 2 is obtained for constructive reasons separately from the upper portion 1 and is successively fixed thereto. The equivalent parts of the two embodiments are marked with the same reference numbers. Obviously, the bridge 20 may be also replaced with a star arrangement having three or four arms, according to the individual requirements. In this case, the apparatus is formed so that it is integral with the root assembly at the end of the operation, as shown in FIGS. 5 and 6.

The insertion of the second embodiment is carried out, through an operation like that already described, by providing in the bone a longitudinal cavity for the insertion of the root assemblies. It is opportune to round off the lower portion 20a of the bridge 20 in order to avoid compression of the bone with a shearing stress.

If the available bony tissue has a limited height, e.g. in consequence of the individual age or the characteristics of the jaw bones, the upper portion 1 that includes the alveolus 3 may be lowered into the lower portion 2 in order to employ partially the alveolus 3 in the bridge 20. Thus, the alveolus 3 will be provided in the central and lower part of the lower portion 2 with a spheric projection that will act as an intermediate support in order to reduce the unit load acting on the bore.

Although only two embodiments are illustrated, it is evident that it is possible to manufacture various devices with a large range of variants that are fitted to different individual conditions. Therefore, not only may any apparatus be provided with a root assembly with several tips, generally two to a maximum of five, but also a bridge may be provided with two or more arms, each with its respective root assembly.

The assemblying of the bridge 20 still provides for the spreading of the tips 11 through the insertion of the little pin 16 by means of the above mentioned instrument 12. It should be noted also that the root assemblies of the bridge 20 can have different heights due to the variable height of the bone so that the root assembly can be embedded at the most suitable depth.

However, the selection of the apparatus most suitable to the various operative conditions, among those of the equipment range according to the present invention, can be easily determined by anyone skilled in the art.

What we claim is:

1. An apparatus for mounting a dental prosthesis, comprising:
    a first pin means for carrying a holder means for supporting at least one tooth, said first pin means having a lower spheric head portion;
    a first body which includes a spheric inner duct means for receiving the lower spheric head portion of the first pin means, said first body having the inner surface of its duct means covered by a layer of an elastomeric material, said first body also having an externally threaded lower end extending downwards;
    a second body including an upper internally threaded portion and a lower end portion, the bottom of this lower end portion being divided in sections forming guide tangs with external tips; and
    a second pin means, to be received inside the lower end portion of the second body, for causing and maintaining the outward rotation of the external tips up to substantially transverse anchoring positions when implanted into fibromucous membrane.

2. Apparatus as in claim 1, wherein the first pin means and its lower spheric head portion are covered by the elastomeric material of the first body.

3. Apparatus as in claim 1, wherein the external surface of the apparatus above the middle plan is substantially cylindrical.

4. Apparatus as in claim 1, wherein there are two to five external tips having at least three sided cross sections and, further, wherein lower edges of the external tips, when inserted in a bone, form with the longitudinal axis of the second body, an angle, not greater than 45°, that can be increased to 90° at the end of the operation.

5. Apparatus as in claim 1, wherein material, preferably titanium, forming the second body is heat treated in order to increase its strength.

6. Apparatus as in claim 1, wherein the upper internally threaded portion, provided in the second body, is counter-threaded for receiving the externally threaded lower end of the first body.

7. Apparatus as in claim 1, comprising a bridge provided with at least two arms, each arm forming a second body, the lower portions of said arms being rounded off so as to avoid compression of a bone.

8. Apparatus as in claim 1, comprising at least two second bodies of equal heights.

9. Apparatus as in claim 1, comprising at least two second bodies of different heights.

10. Method of inserting a dental prosthesis, comprising the steps of:
    incising the gingival fibromucous membrane;
    forming with a drill a cavity in a bone in order to obtain a seat for inserting at least one root assembly of the prosthesis;
    inserting the at least one root assembly in said seat;
    screwing an instrument in said seat of the at least one root assembly so a pin is brought into contact with tangs located at the lower end portion of the at least one root assembly; and
    applying rapidly a force to the pin in order to insert suddenly the pin among the tangs so that external tips of said tangs are simultaneously rotated out and upwards in order to lock said external tips in the bone in an arrangement substantially radial to the longitudinal axis of the at least one root assembly.

* * * * *